(12) United States Patent
Catanzarite

(10) Patent No.: US 10,520,394 B2
(45) Date of Patent: Dec. 31, 2019

(54) ELASTOMERIC DEGRADATION INDICATOR DEVICES, SYSTEMS, AND METHODS

(71) Applicant: LORD Corporation, Cary, NC (US)

(72) Inventor: David M. Catanzarite, Edinboro, PA (US)

(73) Assignee: LORD Corporation, Cary, NC (US)

( * ) Notice: Subject to any disclaimer, the term of this patent is extended or adjusted under 35 U.S.C. 154(b) by 0 days.

(21) Appl. No.: 15/509,356

(22) PCT Filed: Sep. 29, 2015

(86) PCT No.: PCT/US2015/052922
§ 371 (c)(1),
(2) Date: Mar. 7, 2017

(87) PCT Pub. No.: WO2016/054026
PCT Pub. Date: Apr. 7, 2016

(65) Prior Publication Data
US 2017/0248492 A1 Aug. 31, 2017

Related U.S. Application Data

(60) Provisional application No. 62/056,892, filed on Sep. 29, 2014.

(51) Int. Cl.
| | | |
|---|---|---|
| *G01M 13/00* | (2019.01) | |
| *F16F 1/40* | (2006.01) | |
| *G01N 21/88* | (2006.01) | |

(52) U.S. Cl.
CPC ............ *G01M 13/00* (2013.01); *F16F 1/406* (2013.01); *G01N 21/8803* (2013.01); *F16F 2230/0047* (2013.01)

(58) Field of Classification Search
CPC .... G01M 13/00; G01N 21/8803; F16F 1/406; F16F 2230/0047
USPC .............. 267/294, 292; 188/1.11 W, 1.11 R; 152/154.2, 523, 525; 156/110.1
See application file for complete search history.

(56) References Cited

U.S. PATENT DOCUMENTS

| | | | |
|---|---|---|---|
| 3,474,666 A | | 10/1969 | Litzler |
| 3,516,467 A | * | 6/1970 | Sims .................. B60C 11/0309 152/154.2 |
| 3,799,108 A | | 3/1974 | Mosow |
| 4,144,921 A | | 3/1979 | Keiichiro et al. |
| 4,353,227 A | | 10/1982 | Harper et al. |
| 4,432,240 A | | 2/1984 | Adams |

(Continued)

FOREIGN PATENT DOCUMENTS

| | | |
|---|---|---|
| FR | 2342859 | 9/1977 |
| JP | 2008082914 | 4/2008 |

(Continued)

*Primary Examiner* — Pamela Rodriguez

(57) ABSTRACT

The present subject matter relates to devices, systems, and methods for indicating degradation in a component having one or more elastomeric elements. For example, a degradation indicator can include an indicator element in communication with at least a portion of the one or more elastomeric elements, wherein the indicator element is configured to show visible degradation or damage when a specific and predetermined condition of the one or more elastomeric elements is reached.

15 Claims, 3 Drawing Sheets

(56) References Cited

U.S. PATENT DOCUMENTS

| | | | |
|---|---|---|---|
| 4,906,917 A | | 3/1990 | Olness et al. |
| 5,261,508 A | | 11/1993 | Kikuchi |
| 5,962,778 A | * | 10/1999 | Billieres ............... G01M 17/02 152/154.2 |
| 5,979,628 A | | 11/1999 | Lampe |
| 5,980,668 A | * | 11/1999 | Slingluff ................ B60C 11/24 152/154.2 |
| 6,634,222 B2 | * | 10/2003 | O'Brien ................. B60C 11/24 152/154.2 |
| 6,775,877 B1 | | 8/2004 | Broszniowski |
| 7,278,369 B2 | | 10/2007 | Kelley et al. |
| 2006/0261617 A1 | | 11/2006 | St. Germain |
| 2008/0121170 A1 | | 5/2008 | Larsen et al. |
| 2011/0288838 A1 | | 11/2011 | Hamantani et al. |
| 2012/0082422 A1 | | 4/2012 | Sarchi et al. |
| 2013/0036791 A1 | | 2/2013 | Shibata |

FOREIGN PATENT DOCUMENTS

| | | |
|---|---|---|
| WO | 00/35726 | 6/2000 |
| WO | 05/090821 | 9/2005 |
| WO | 13/130755 | 9/2013 |

\* cited by examiner

ELASTOMERIC DEGRADATION INDICATOR DEVICES, SYSTEMS, AND METHODS

PRIORITY CLAIM

The present application claims the benefit of U.S. Provisional Patent Application Ser. No. 62/056,892, filed Sep. 29, 2014, the disclosure of which is incorporated herein by reference in its entirety.

TECHNICAL FIELD

The subject matter disclosed herein relates generally to components having elastomeric elements. More particularly, the subject matter disclosed herein relates to degradation indicators for elastomeric elements.

BACKGROUND

In many components that contain elastomeric elements, it can be difficult to inspect parts because of their installation location and/or their assembly layout. In particular, in configurations where layers of elastomeric material are arranged between shims or partitions and/or are located in small areas of the component, there is often a further practical difficulty in inspecting such layers. Furthermore, even where inspection is possible for portions of an elastomeric element, in some cases it is also difficult to know whether the condition of the inspected portion is representative of the condition of the component as a whole since predicting where the damage of the elastomer will initiate first depends on the working conditions of the parts and on the strain and stress level distributions.

As a result, it would be advantageous for components that contain elastomeric elements to be configured such that the condition of the elastomeric elements could be easily inspected, thereby allowing the amount of degradation or damage experienced by the components to be readily identified, which can enable users of the components to more accurately estimate when the components will need to be repaired and/or replaced.

SUMMARY

In accordance with this disclosure, devices, systems, and methods for indicating degradation in a component having one or more elastomeric elements are provided. In one aspect, a degradation indicator for a component having one or more elastomeric elements is provided. In some embodiments, the degradation indicator includes an indicator element in communication with at least a portion of the one or more elastomeric elements, wherein the indicator element is configured to show visible degradation or damage when a specific and predetermined condition of the one or more elastomeric elements is reached.

In another aspect, a method for making a degradation indicator for a component having one or more elastomeric elements is provided. In some embodiments, this method includes coupling an indicator element to at least a portion of the one or more elastomeric elements and configuring the indicator element to show visible degradation or damage when a specific and predetermined condition of the one or more elastomeric elements is reached.

In yet another aspect, a method for inspecting a component having one or more elastomeric elements is provided. In some embodiments, such a method includes visually inspecting an indicator element in communication with at least a portion of the one or more elastomeric elements and repairing or replacing the one or more elastomeric elements when the indicator element shows visible degradation or damage corresponding to a specific and predetermined condition of the one or more elastomeric elements.

Although some of the aspects of the subject matter disclosed herein have been stated hereinabove, and which are achieved in whole or in part by the presently disclosed subject matter, other aspects will become evident as the description proceeds when taken in connection with the accompanying drawings as best described hereinbelow.

DETAILED DESCRIPTION

The present subject matter provides devices, systems, and methods for indicating degradation in a component having one or more elastomeric elements. In particular, the present subject matter provides devices, systems, and methods in which an indicator element is purposely designed to show degradation or damage when a specific and predetermined condition is reached with respect to one or more elastomeric elements to which the indicator element is coupled. In this regard, the operation of the indicator element disclosed herein can be likened to the principle of electrical fuses. As is understood by those having skill in the art, a fuse is a device that works as a sacrificial component used to protect the main system from over-current conditions. By analogy, the indicator element is designed to "blow" when specific conditions are reached in order to protect the integrity of the rest of the system and warn the operator that damage has initiated.

Figure 1:
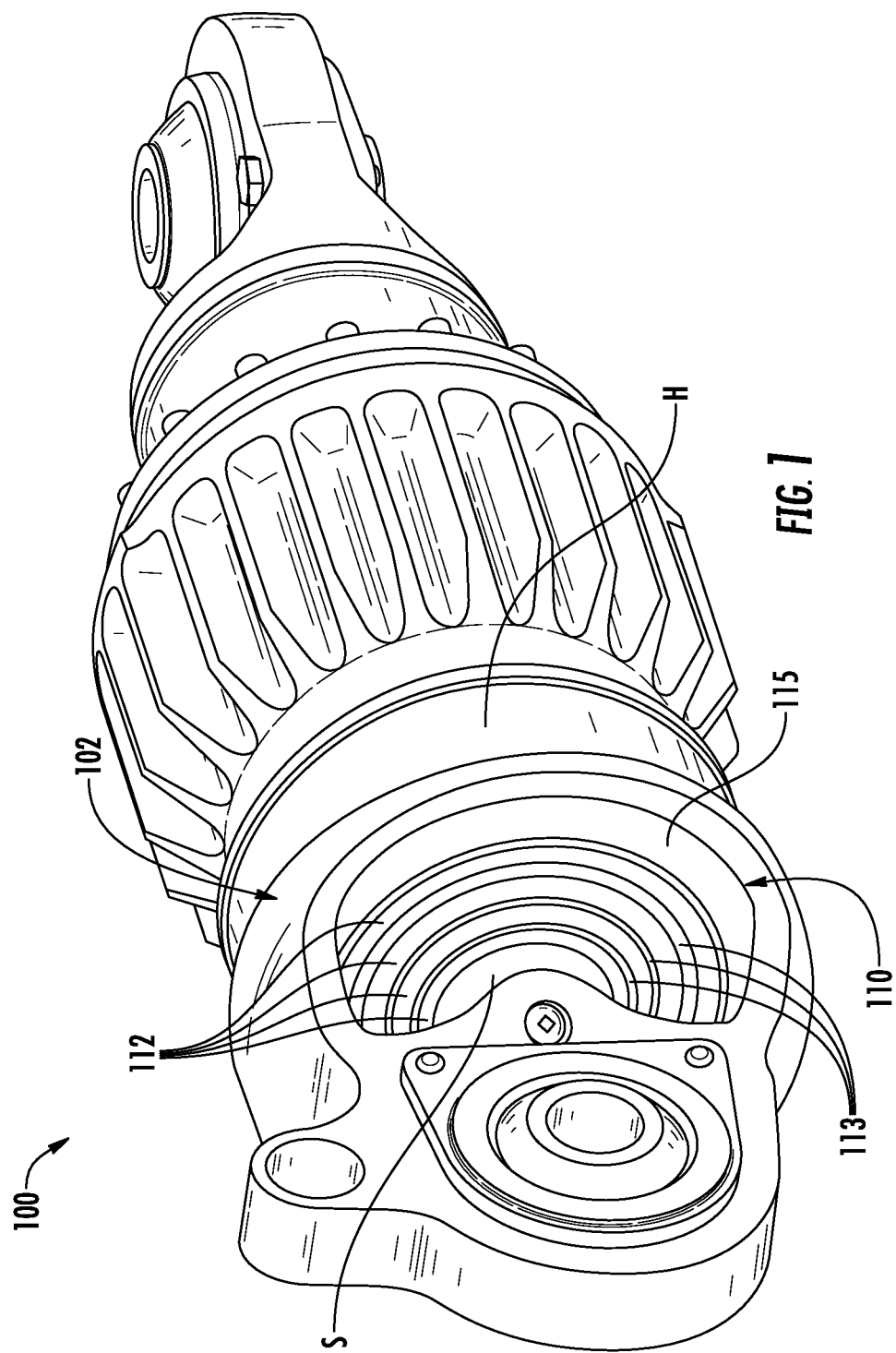
FIG. 1 is a perspective side view of a development damper having an elastomeric degradation indicator according to an embodiment of the presently disclosed subject matter.
Figure 2:
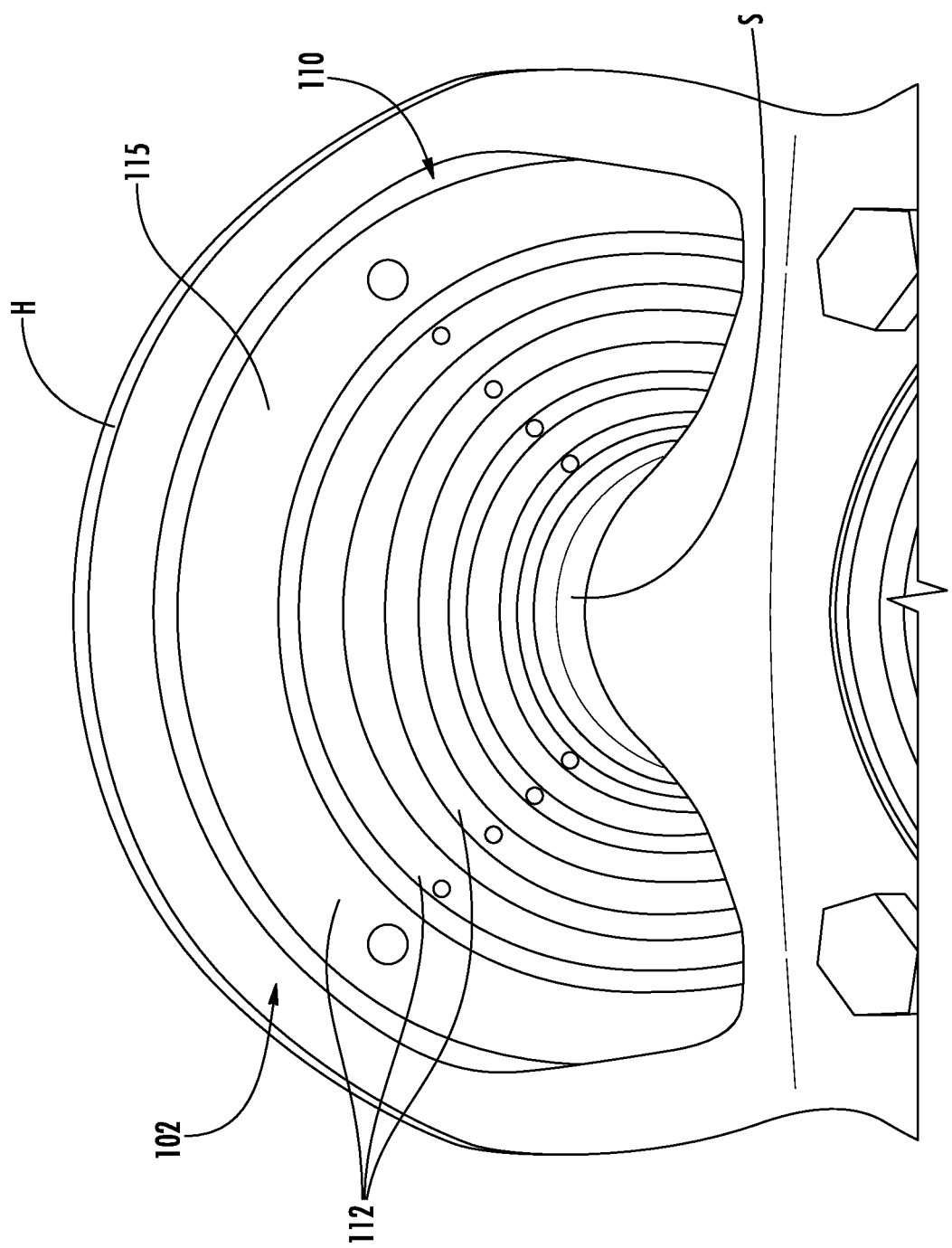
FIG. 2 is a side view of a component containing an elastomeric element, wherein an elastomeric degradation indicator is purposely designed to show degradation or damage when a specific and predetermined condition is reached according to an embodiment of the presently disclosed subject matter.

In the particular example illustrated in FIGS. 1 and 2, for instance, an elastomer-containing component, generally designated 100, includes one or more elastomeric material element, generally designated 110. In some embodiments, for example, elastomer element 110 comprises a plurality of elastomeric material layers 112. In the particular configuration shown in FIGS. 1 and 2, for example, component 100 is a damper having a plurality of elastomeric material layers 112 arranged in an array of substantially annular sections arranged concentrically between a housing H and a shaft S, with one or more metal shims or other stiffeners 113 provided between adjacent elastomeric material layers 112 (e.g., to help control the in-plane and out-of-plane stiffness). Although the particular arrangement shown in FIGS. 1 and 2 is used herein to describe one exemplary application of the present subject matter, those having skill in the art should recognize that the principles discussed herein may be applied to any of a variety of other elastomer-containing components beyond this particular configuration. In particular, even though the figures depict various embodiments of component 100 having this arrangement of elastomer element 110 being divided into concentric annular sections, those having skill in the art will recognize that the principles discussed herein are not limited to annular/tubular geometries. Rather, the described embodiments and use of degradation-indicating elements may be suitable in any application in which elastomer elements experiencing repetitive relative motion between two members as described herein are utilized.

In this regard, regardless of the particular configuration of elastomer element 110, component 100 includes an indicator element 115 comprising an elastomeric material that exhibits degradation and/or damage corresponding to the condition of the one or more elastomeric element 110. For example, in some embodiments, indicator element 115 is an area of elastomer element 110 itself that is used as a warning indicator before significant degradation or damage of the elastomeric material would occur. In the particular configuration shown in FIGS. 1 and 2, for example, indicator element 115 is provided on the outermost layer of elastomer element 110. In this arrangement, elastomer element 110 can easily be visually inspected to determine whether high levels of degradation or any damage have occurred in the elastomeric material contained therein (e.g., in one or more of elastomeric material layers 112). As it can be observed, in some embodiments, the visibility of the outermost layer compared to the inner ones is much greater, thus facilitating the detection of any damage that should occur.

Regardless of the way in which indicator element 115 is configured with respect to elastomer element 110, indicator element 115 is purposely designed to show degradation or damage when a specific and predetermined condition is reached with respect to one or more elastomer element 110 to which indicator element 115 is coupled. In particular, the condition triggering the degradation and/or damage of indicator element 115 is defined during the initial design phase of the component. In some embodiments, for example, this trigger condition is related to the number of accumulated hours of use, the strain levels, the stress levels, or any of a variety of other parameters that characterize the operating condition of component 100. For example, in some embodiments, the specific and predetermined condition under which indicator element 115 is worn and/or damaged is a specific and predetermined value of stress and/or strain in the one or more elastomeric elements, and these stress or strain values correspond to a selected value at which replacement of elastomer element 110 is recommended.

In this way, in some embodiments, a primary function of indicator element 115 is to act as an indicator by first showing a sign of degradation in an area that is very inspection friendly. For example, in some embodiments, indicator element 115 is positioned in an area of component 100 that is substantially visually unobstructed by other elements of component 100. Accordingly, in some embodiments, component 100 includes at least one inspection port 102, such as is illustrated in FIGS. 1 and 2, which improves the ability to inspect the condition of elastomer element 110. In this configuration, at least a portion of elastomer element 110 is visible without requiring any elements of component 100 to be detached, moved, disassembled, or otherwise modified to allow observation of indicator element 115.

In addition, in some embodiments, indicator element 115 is positioned in an area of component 100 that will not affect component performance. In other words, degradation and/or damage to indicator element 115 does not significantly diminish normal operability of component 100. In this way, indicator element 115 works as detection device, which can be used to facilitate the inspection of elastomer element 110. Use of indicator element 115 thereby allows an increase in the level of control and the inspection of the elastomeric material of elastomer element 110 during the working life of component 100. This feature can be particularly desirable in configurations in which the elastomeric element 110 comprises one or more elastomeric material layers 112 that are positioned in layers between shims or partitions 113 and/or are in small areas of the package. In such configurations, indicator element 115 reduces the unpredictability of the damage initiation location in an elastomeric configuration where there are more than one layer stacked up in a laminated package.

In addition, in some embodiments, indicator element 115 is designed and used to not only identify that degradation and/or damage has reached an indicated level, but indicator element 115 further is configured to be in communication with the area of elastomer element 110 where the degradation or damage will be induced first. In particular, in some embodiments, component 100 is designed such that indicator element 115 is placed at a particular location at which damage is expected to occur first. In some embodiments, for example, indicator element 115 is designed to include one or more structural feature 116 (e.g., a designed flaw, a weak spot, or a stress concentration) that is configured to accelerate the rate at which degradation or damage is incurred under normal operating loads on the portion of elastomer element 110. As a result, indicator element 115 addresses the problem regarding the uncertainty where damage initiation may occur on an elastomer-containing component.

Figure 3A:
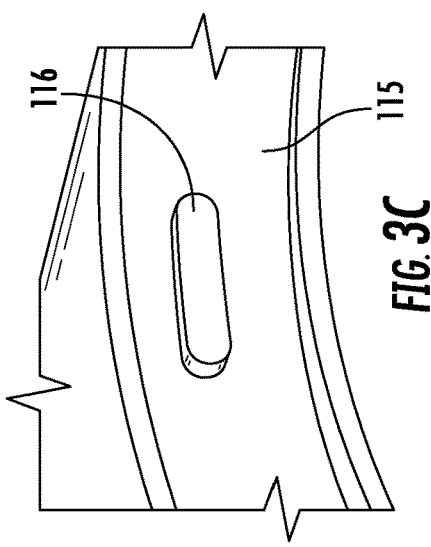
FIGS. 3A through 3E are side detail views of an elastomeric degradation indicator having various configurations for a structural feature that is configured to accelerate the rate at which degradation or damage is incurred under normal operating loads on the portion of an elastomer element according to embodiments of the presently disclosed subject matter.
Figure 3B:
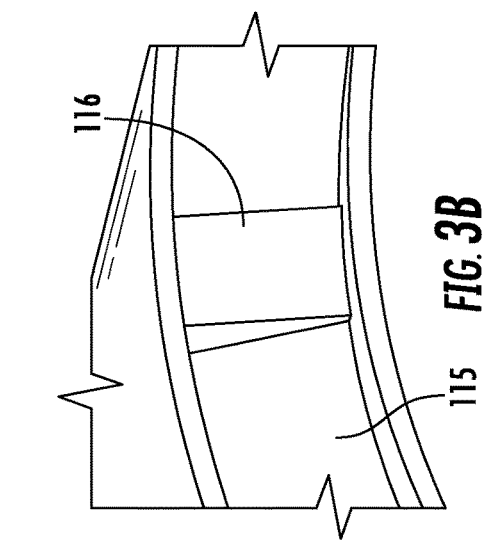
Figure 3C:
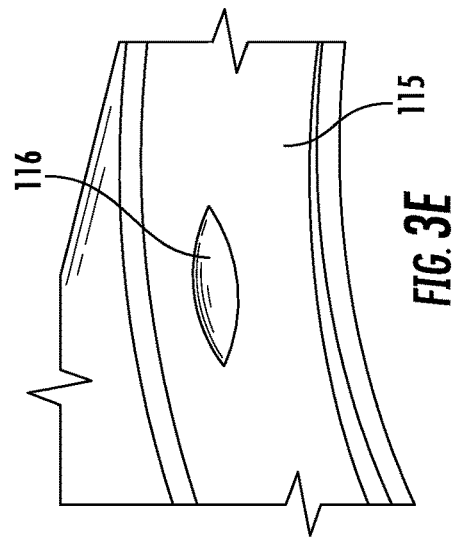
Figure 3D:
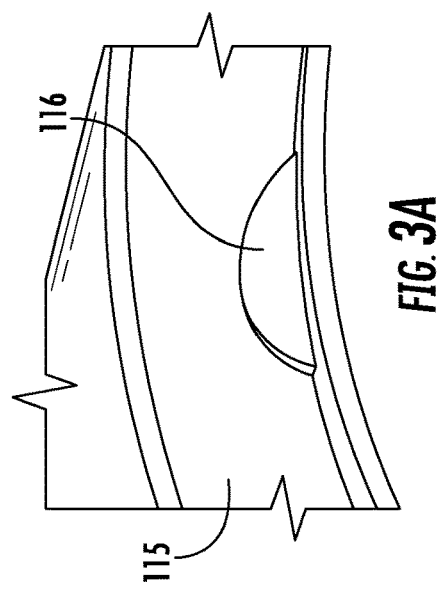
Figure 3E:
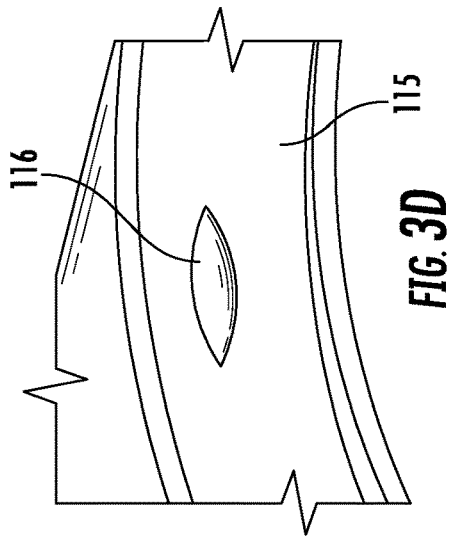

In particular, FIG. 3A illustrates a configuration in which structural feature 116 is a buttress that protrudes from indicator element at a position that is substantially adjacent to a surrounding structural element (e.g., one of shims or partitions 113). FIG. 3B illustrates a configuration in which structural feature 116 is a substantially rectangular fuse block that extends across a portion of indicator element 115. FIG. 3C illustrates a configuration in which structural feature 116 is a substantially oval-shaped button that protrudes from indicator element 115. FIG. 3D illustrates a configuration in which structural feature 116 is a protrusion having a more tapered shape terminating on each end at a point. Finally, FIG. 3E illustrates a configuration in which structural feature 116 has a similar shape to the protrusion shown in FIG. 3D, but in this configuration structural feature 116 is recessed into indicator element 115. In any of these exemplary arrangements, structural feature 116 acts as a stress concentrator that accelerates the rate at which the elastomeric material is worn or damaged such that such degradation or damage is apparent at indicator element 115 prior to the remainder of elastomer element 110 being compromised. In some embodiments, the rate of degradation is designed to be only marginally accelerated relative to the remainder of elastomer element 110 so that indicator element 115 does not indicate that degradation or damage has been incurred too long in advance of a desired replacement interval for elastomer element 110.

In such configurations where indicator element 115 is positioned in in communication with the area of elastomer element 110 where the degradation or damage will be expected to be induced first, the operator can conduct a more efficient inspection to identify when damage occurs since they can inspect the exact location where the initiation of significant degradation or damage on the elastomeric material is expected. Further in this regard, in some embodiments, structural feature 116 is designed such that it resembles a visual icon that clearly identifies itself as indicator element 115 (e.g., as illustrated in FIGS. 3A through 3E, structural feature 116 can be configured to look like a fuse or gauge or any symbol that represents the intent of the indicator). Those having ordinary skill in the art will understand how to design and manufacture the aforementioned structural feature 116.

The present subject matter can be embodied in other forms without departure from the spirit and essential characteristics thereof. The embodiments described therefore are to be considered in all respects as illustrative and not restrictive. Although the present subject matter has been described in terms of certain preferred embodiments, other embodiments that are apparent to those of ordinary skill in the art are also within the scope of the present subject matter.

What is claimed is:

1. A degradation indicator for a component having one or more elastomeric elements, the degradation indicator comprising:
    an indicator element in communication with at least a portion of the one or more elastomeric elements;
    wherein the indicator element is positioned to show a visible degradation or damage when a specific and predetermined condition of the one or more elastomeric elements is reached;
    wherein the indicator element is in communication with a portion of the one or more elastomeric elements that is positioned to experience damage first within the one or more elastomeric elements, the indicator element comprises at least one structural feature that is degraded or damaged at an accelerated rate under normal operating loads on the portion of the one or more elastomeric elements.

2. The degradation indicator of claim 1, wherein the indicator element comprises a portion of the one or more elastomeric elements.

3. The degradation indicator of claim 1, wherein the at least one structural feature is selected from the group consisting of a designed flaw, a weak spot, or a stress concentration.

4. The degradation indicator of claim 1, wherein the specific and predetermined condition comprises a specific and predetermined value of stress and/or strain in the one or more elastomeric elements.

5. The degradation indicator of claim 4, wherein the specific and predetermined value of stress and/or strain corresponds to a selected value at which replacement of the one or more elastomeric elements is recommended.

6. The degradation indicator of claim 1, wherein the indicator element is positioned in an area of the component that is substantially visually unobstructed by other elements of the component.

7. The degradation indicator of claim 1, wherein the indicator element is positioned in an area of the component where degradation and/or damage to the indicator element does not significantly diminish normal operability of the component.

8. The degradation indicator of claim 1, wherein the component comprises a damper.

9. A method for making a degradation indicator for a component having one or more elastomeric elements, the method comprising:
    coupling an indicator element to at least a portion of the one or more elastomeric elements;
    configuring the indicator element to show a visible degradation or damage when a specific and predetermined condition of the one or more elastomeric elements is reached;
    positioning the portion of the one or more elastomeric elements to which the indicator element is coupled to experience damage first within the one or more elastomeric elements; and
    introducing at least one structural feature that degrades or is damaged at an accelerated rate under normal operating loads on the portion of the one or more elastomeric elements.

10. The method of claim 9, wherein coupling an indicator element to at least a portion of the one or more elastomeric elements comprises coupling an elastomeric material in communication with the one or more elastomeric elements.

11. The method of claim 9, wherein introducing at least one structural feature comprises introducing one or more features selected from the group consisting of a designed flaw, a weak spot, or a stress concentration.

12. The method of claim 9, wherein configuring the indicator element to show visible degradation or damage when a specific and predetermined condition of the one or more elastomeric elements is reached comprises configuring the indicator element to show visible degradation or damage when a specific and predetermined value of stress and/or strain is reached in the one or more elastomeric elements.

13. The method of claim 12, wherein the specific and predetermined value of stress and/or strain corresponds to a selected value at which replacement of the one or more elastomeric elements is recommended.

14. The method of claim 9, wherein coupling the indicator element to at least a portion of the one or more elastomeric elements comprises positioning the indicator element in an area of the component that is substantially visually unobstructed by other elements of the component.

15. The method of claim 9, wherein coupling the indicator element to at least a portion of the one or more elastomeric elements comprises positioning the indicator element in an area of the component where degradation and/or damage to the indicator element does not significantly diminish normal operability of the component.

* * * * *